United States Patent [19]

Wegman

[11] Patent Number: 4,990,654
[45] Date of Patent: Feb. 5, 1991

[54] PRODUCTION OF ACETATE ESTERS FROM ALCOHOLS USING RHODIUM COMPLEX CATALYSTS

[75] Inventor: Richard W. Wegman, South Charleston, W. Va.

[73] Assignee: Union Carbide Chemicals and Plastics Company Inc., Danbury, Conn.

[21] Appl. No.: 462,888

[22] Filed: Jan. 4, 1990

Related U.S. Application Data

[63] Continuation of Ser. No. 796,495, Nov. 8, 1985, abandoned, which is a continuation-in-part of Ser. No. 641,206, Aug. 16, 1984, abandoned.

[51] Int. Cl.$^5$ .................. C07C 67/36; C07C 69/14
[52] U.S. Cl. ............................ 560/232; 556/18
[58] Field of Search ............................ 560/232

[56] References Cited

U.S. PATENT DOCUMENTS

| | | | |
|---|---|---|---|
| 3,769,329 | 10/1973 | Paulik et al. | 562/519 |
| 3,856,856 | 12/1974 | Nozaki | 560/232 |
| 4,134,912 | 1/1979 | Naglieri et al. | 562/579 |
| 4,166,189 | 8/1979 | Wald et al. | 560/232 |
| 4,212,989 | 7/1980 | Isshiki et al. | 560/232 |
| 4,250,329 | 2/1981 | McVicker et al. | 560/232 |
| 4,563,309 | 1/1986 | Wegman | 502/166 X |
| 4,670,570 | 1/1987 | Wegman et al. | 552/18 |

FOREIGN PATENT DOCUMENTS

| | | | |
|---|---|---|---|
| 45637 | 2/1982 | European Pat. Off. | 562/517 |
| 51-80813 | 7/1975 | Japan . | |
| 55-160743 | 12/1980 | Japan . | |
| 56-104839 | 8/1981 | Japan . | |
| 1286224 | 8/1972 | United Kingdom | 562/517 |
| 1293193 | 10/1972 | United Kingdom | 562/606 |
| 1326014 | 8/1973 | United Kingdom | 562/519 |
| 0117575 | 9/1984 | United Kingdom . | |

OTHER PUBLICATIONS

Chemical Abstracts, vol. 98, No. 11, 14th Mar. 1983, p. 679, Abstract No. 100166a, Columbus, Ohio, U.S.; R. Uson et al.: "Bidentate Amine N–Oxides and Phosphine Oxides as Ligands in Rhodium(I) Chemistry", & J Organomet, Chem. 1982, 240(4), 429–39.

*Primary Examiner*—Vivian Garner
*Attorney, Agent, or Firm*—Reynold J. Finnegan

[57] ABSTRACT

A process for the production of acetate esters by the catalytic reaction of an alcohol of the formula ROH and carbon monoxide in contact with a homogeneous catalyst system of rhodium metal atom, a phosphorus containing ligand in which there is present at least one oxo (=O) oxygen atom attached to a phosphorus atom or a carbon atom to form a Z group and the

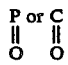

group is located at least one carbon atom removed and preferably from 2–4 carbon atom removed from the phosphorus atom of the molecules represented by the formulas

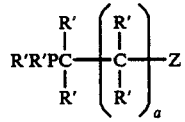 (V)

or

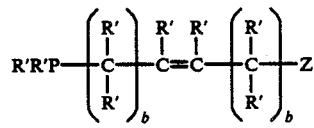 (VI)

and a halogen promoter, under mild reaction conditions, wherein R' is H, aryl, alkaryl, aralkyl or alkyl, and wherein 1 or more of said R' groups can be substituted with a Z group but not more than 3 of said R' groups in the molecule are so substituted; a is an integer from 0–4; b is an integer from 0–3; and Z is P(O)R'R'; —C(O)OR" or C(O)R", wherein R" is R'; and wherein ROH is methanol or a mixture of methanol and at least one higher alcohol.

2 Claims, No Drawings

PRODUCTION OF ACETATE ESTERS FROM ALCOHOLS USING RHODIUM COMPLEX CATALYSTS

This application is a continuation of prior U.S. application Ser. No. 796,495 filing data 11/8/85 now abandoned which is a continuation-in-part of application No. 641,206 filing date 8/16/84 now abandoned.

BACKGROUND OF THE INVENTION

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties. however, have resided in the ability to carry out any one of these chosen reactions to produce the desired compound at acceptable efficiency, conversion rate and selectivity.

In almost all instances the reaction is generally catalyzed using a Group VIII transition metal compound as the catalyst and a halogen as the promoter. It is known that many other metal compounds and promoters can be used. In addition, the prior art has disposed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators.

The prior art has taught that a wide variety of Group VIII metals and a halide promoter will catalyze the carbonylation of methanol to methyl acetate. For most Group VIII metals the catalyst system requires extremely high operating pressures. Several patents describing such processes are discussed hereafter.

U.S. Pat. No. 4,212,989, issued to Isshiki et al.. on July 15 1980, describes a process for producing carboxylic acids or their esters by reacting an alcohol or an ether with carbon monoxide using a Group VIII metal catalyst and an iodine promoter. The reference contains no disclosure or suggestion of the production of acetate esters employing a specific rhodium complex under mild reaction conditions.

Japanese patent publication 55-160743. filed by Mitsubushi and published on Dec. 13, 1980 discloses reaction of methanol with a mixture of syn gas and an aluminum catalyst to produce methyl acetate and methyl formate.

The catalyst is charged as aluminum acetylacetonate or the like. Halide promoters are not required. The reaction is typically carried out at pressures from 1700 to 3000 psi with the ratio of hydrogen to carbon monoxide ranging from 1:1 to 0.1:1.

U.S. Pat. No. 4,166,189 issued Aug. 28, 1979 discloses a process for preparing branched methyl esters by the reaction of methanol with carbon monoxide in the presence of a zinc iodide catalyst. Metal acetate was observed only in trace amounts, with the principal products being methyl pivalate and methyl-2,2,3,3,-tetramethylbutyrate. The carbon monoxide partial pressure in the reaction mixture is said to be preferably greater than 1000 psia and the reaction temperature is most preferably from 200 to 280° C. There was no co-feed of another alcohol with the methanol.

Japanese Patent Publication No. 56-104839, filed by Kurrary and published on Aug. 20, 1981 discloses that methyl acetate may be obtained by reacting methanol and carbon monoxide employing a heterogenous catalyst, which includes nickel and/or cobalt-rare earth oxide-and a metal from the platinum group. The rate of methyl acetate formation is very low, usually much less than 1.0 mole per hour and there is no disclosure of co-feeding an alcohol with the methanol.

U.S. Pat. No. 3,856,856, issued Dec. 24, 1974 discloses that methyl acetate may be formed by reacting methanol with carbon monoxide in the presence of a catalyst of the formula Co—I—Pt—$ER_3$, wherein E is N, P, As and R is an organic moiety. Operating temperatures are generally preferred to be from 100–200° C. and preferred operating pressures are in the order of 1000 to 4000 psig. The rate of methyl acetate production is less than 1 mole per liter per hour and there is no disclosure of employing mixtures of different alcohols for the alcohol feed.

Japanese Patent Publication 51-80813, filed by Mitsui Petro Chemical was published on July 15, 1975 and relates to forming methyl acetate by reacting methanol with carbon monoxide employing a Re-I catalyst. It was reported that at 200° C. and 1100 psi the methyl acetate production rate was 1.0 mole per liter per hour and the selectivity was above 40%.

U.S. Pat. No. 4,134,912. issued Jan. 16, 1979 teaches production of methyl acetate by the reaction of methanol with carbon monoxide in the presence of a Ni—Sn—$CH_3I$ catalyst. Although it is stated that a wide range of temperatures is suitable it is disclosed that best results are employed when the reaction temperature is from 125–225° C. The process is said to be carried out at partial pressures from 1 to 10,000 psi, but in the actual results reported, the reaction pressure was maintained at from 350–500 psig.

U.S. Pat. No. 4,250,329 issued Feb. 10, 1981 discloses preparation of esters by the reaction of an alcohol with carbon monoxide in the presence of a halide promoter and a catalyst of the general formula: $BxMN[M'(CO)_a(L)_b]_2$, wherein N is a Group II A metal; Bx is a Lewis base, such as pyridine or THF; M' is a Group VI, VII or VIII metal; L is a derivative of cyclopentadiene and/or $BR_3$, where B is N, P, As, or Sb and R is an organic alkyl. That catalyst is different from the novel rhodium catalyst employed herein.

It is also said in U.S. Pat. No. 4,250,329 that where the carbon monoxide pressure ranges from 1000 to 4000 psig. ester formation is favored. Such reaction conditions especially reaction pressure, are rather harsh. It is further said that reaction temperatures from 100–200° C. favor ester formation. It is also noted that the process is applicable to production of unsymmetrical esters, such as by mixing methanol and isopropanol to yield methyl acetate, isopropyl acetate and small amounts of methyl propionate and methyl isopropionate. Such reaction conditions, especially reaction pressure are rather harsh.

U.S. Pat. No. 3,769,329 issued Oct. 30, 1973 relates to forming acetic acid by carbonylating methanol with a Rh-I In several examples, notably Examples 27-29, a process for producing methyl acetate is illustrated. In those examples the reaction temperature was 175° C. and the reaction pressure, 500 psig. At such conditions well beyond those of the instant invention the methyl acetate rate was about 3 % moles per liter per hour and selectivity was 90%.

The above-noted patents demonstrate that a wide variety of Group VIII metals and a halide promoter will catalyze the carbonylation of methanol to methyl acetate. In general, however such catalysts require high operating pressures, usually, on the order of from 3000 to 5000 psi. A rhodium catalyst functions at somewhat lower operating pressures on the order of 500 psi but only when reaction temperatures are maintained on the order of 180° C.

Typical prior art processes employing various Group VIII catalysts to produce acetate esters require rather harsh reaction conditions of temperature and pressure to obtain satisfactory yields of products. Such r(R)action conditions require use of expensive reactors engender excessive energy cost, often lead to undesired by-products and cause excessive corrosion problems.

SUMMARY OF THE INVENTION

A process for the production of acetate esters has been discovered. The process can produce esters of the formula $CH_3C(O)OR$, wherein R is a monovalent hydrocarbyl group, and preferably an alkyl group having 1 to 10 carbon atoms. The process includes the catalytic reaction of an alcohol of the formula ROH and carbon monoxide in contact with a homogeneous catalyst system at mild reaction conditions.

As employed herein, ROH denotes methanol a mixture of methanol and a higher alcohol, or a mixture of methanol and at least two different higher alcohols. Accordingly. ROH is methanol or a mixture of methanol and at least one higher alcohol. If methanol is the sole alcohol of the feed, methyl acetate is formed. If methanol and a higher alcohol, as ethanol is employed, then the esters formed will be methyl acetate and ethyl acetate. If a mixture of higher alcohols is employed, as ethanol and propanol, for example, then the esters formed inter alia will be a mixture of methyl acetate, ethyl acetate and propyl acetate.

It is important to note that if the higher alcohols are employed with methanol, that they will not become carbonylated.

The catalyst system consists essentially of rhodium metal atom and a phosphorus containing ligand in which there is present at least one oxo (=O) oxygen atom attached to a phosphorus atom or a carbon atom to form a Z group and the

group in said Z group is located at least one carbon atom removed and preferably from 2-4 carbon atoms removed from the phosphorus atom of the molecules represented by the formulas

or

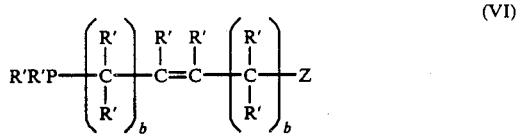

and a halogen-containing compound as a promoter, wherein R' is hydrogen or unsubstituted or substituted (e.g. halogen, nitro, amino, etc.) aryl, aralkyl or alkaryl having from 6 to 10 ring carbon atoms and the alkyl moiety of the aralkyl or alkaryl group has from 1 to 10 carbon atoms and preferably 1 to 4 carbon atoms; or alkyl having from 1 to 10 carbon atoms and preferably 1 to 4 carbon atoms; and wherein 1 or more of said R' groups can be substituted with a Z group but not more than 3 of said R' groups in the molecule are so substituted; a is an integer from 0–4; b is an integer from 0–3; and Z is a member selected from the group consisting of

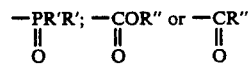

wherein R" is R'. R' can be the same or different.

The reaction conditions are mild, usually at reaction temperatures less than about 130° C. and at reaction pressure less than about 250 psig.

Under catalytic conditions it is understood that a novel monocarbonyl rhodium complex of the formula A:

$$Rh(CO)X(R'R'(GZ)) \qquad [A]$$

wherein X is halogen and R' and Z are as before, and wherein G represents the two

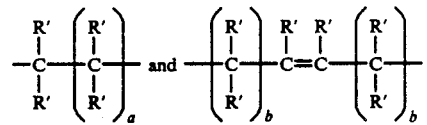

groups of formulas and is formed in-situ.

The novel rhodium complex of the invention has been synthesized, isolated and characterized. The synthesized rhodium complex may be prepared in advance and used in place of the in-situ formed catalyst.

The Formula A rhodium complex is understood to be subject to the addition of a second mole of carbon monoxide to form a second catalytic dicarbonyl rhodium complex of Formula B and having the general formula:

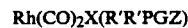

$$Rh(CO)_2X(R'R'PGZ) \qquad [B]$$

The Formula B rhodium complex can be prepared in advance of the process rather than being formed in-situ from Formula [A].

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amount of reactants the catalyst converts to product per unit of time, generally expressed in g. mole per liter per hour (g mole/1/hr) or mole per hour (Mhr$^{-1}$)

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms. promoters and activators, in many cases with diverse other components added. Though these catalyst systems are effective they usually require rather harsh reaction conditions and, accordingly improvement is always desirable. Other factors having an impact on the process are the reaction temperature and reaction pressure. In the past it was generally thought necessary to increase these variables to improve overall selectivity and conversion.

The present invention is based on the unexpected and unpredictable discovery that the herein defined rhodium-catalyst systems which contain the specifically defined ligands produce acetate esters from alcohols of the formula ROH and carbon monoxide at unexpectedly high efficiency, selectivity and conversion rates at mild reaction conditions. Optionally, a solvent and/or diluent can also be present.

In the process of our invention certain alcohols are reacted with carbon monoxide in the presence of the inventive catalyst system. This system produces commercially desirable acetate esters at unexpectedly high efficiency, conversion rate and selectivity, with a minimum of by-products and under mild reaction conditions. The overall reaction that occurs in the production of acetate esters is theoretically:

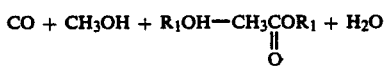

In the above formula $R_1$ is a monovalent hydrocarbyl group. It can be an alkyl group having from 1 to 30 carbon atoms, preferably from 1 to 15 carbon atoms, and most preferably from 1 to 5 carbon atoms; an alkenyl group having from 2 to 30 carbon atoms, preferably from 2 to 15 carbon atoms and most preferably from 2 to 5 carbon atoms; or an aryl, aralkyl or alkaryl group having 6 or 10 ring carbon atoms, e.g., phenyl and naphthyl, with from 1 to 10 carbon atoms, preferably 1 to 4 carbon atoms, in the alk-moiety therof. The R group can be linear or branched and it can be unsubstituted or substituted with groups which will not have an adverse effect on the reaction; further; the alkenyl groups can contain more than one unsaturated bond. Among the preferred alcohols are methanol, ethanol and the propanols, butanols and pentanols, with the most preferred ones being methanol and ethanol.

In general the alcohol (ROH) is a mixture of methanol and at least one higher alcohol of the formula $R_1OH$. The mole ratio of methanol to the total of such higher alcohol(s) can vary over a wide range at the discretion of the practitioner; typically from about 20:1 to 1:20.

The rhodium component of the catalyst system can be supplied from any number of sources, many of them are known to those of ordinary skill in the art. Thus, it is not necessary for an understanding thereof to specifically enumerate every suitable type and every specific compound since any of the known rhodium compounds can be used.

The essential rhodium component of the catalyst system of the present invention may be provided by introducing into the reaction zone a compound of rhodium or may be provided by introducing into the reaction zone, rhodium. Among the materials which may be charged to the reaction zone to provide the rhodium component of the catalyst system of the present invention are rhodium metal, rhodium salts and oxides organo rhodium compounds coordination compounds of rhodium,and the like. Specific examples of materials capable of providing the rhodium constitutent of the catalyst system of the present invention may be taken from the following non-limiting partial list of suitable materials.

$RhCl_2$
$RhBr_3$
$RhI_2$
$RhCl_3 \cdot H_2O$
$RhBr_3 \cdot H_2O$
$Rh_2(CO)_4Cl_2$
$Rh_2(CO)_4Br_2$
$Rh_2(CO)_4I_2$
$Rh_2(CO)_8$
Rh metal
$Rh(NO_3)_3$ [(n-$C_4H_9)_4N$][$Rh(CO_2X_2$]where X=Cl—, Br—, I—
[(n—$C_4H_9)_4As]_2[Rh(CO)_2Y_4$]where X=Cl—, Br—, I—
[(n—$C_4H_9)_4P$][$Rh(CO)I_4$]
$Rh_2O_3$
[$Rh(C_3H_4)_2Cl]_2$
$K_4Rh_2Br_2(SnBr_3)_4$
$K_4Rh_2I_2(SnI_2)_4$ The rhodium metal atom concentration can vary over a wide range. Enough metal atom must be present to achieve reasonable reaction rates: however, an excess may, on occasion, result in undesired by-products formation. The mole ratio of rhodium atom to alcohol can vary from 1:25 to 1:20000. the preferred range is from about 1:40 to 1:1000 with the most preferred range being from about 1:100 to 1:500. The amount used is not a critical feature in this invention and higher rhodium concentrations are acceptable but ar influenced by economic considerations.

In general the rate of reaction increases with increasing rhodium concentration. For most purposes it is sufficient to employ a rhodium concentration from about 0.0001 to 1 mole per liter, preferably from about 0.01 to 0.1 mole per liter, although higher or lower concentrations may be utilized, depending, in part, upon economic considerations.

The second component of the catalyst system is a halide containing compound as a promoter.

The halide component of the catalyst can be a halogen compound containing iodine, bromine or chlorine or two or more of the same, or the elemental halogen per se. or any mixtures of compounds and/or elements. Their identities are well known to those of ordinary skill in this art.

The preferred halogen compound is iodine or inorganic or organic compounds containing the iodine atom. As indicated, the suitable halogen compounds are well known to those of average skill in this art and a complete listing is not necessary for their comprehension.

Illustrative thereof there can be mentioned barium iodide, hydriodic acid, cobalt iodide, potassium iodide lithium iodide, sodium iodide calcium iodide, ammonium iodide, methyl iodide, ethyl iodide propyl iodide 2-ethylhexyl iodide, n-decyl iodide acetyl iodide propionyl iodide; the organic ammonium iodides of the formula R'''$_4$NI and the organic phosphonium iodides of the formula R'''$_4$PI in which R''' is alkyl, saturated or unsaturated substituted or unsubstituted, having from 1 to about 10 carbon atoms or aryl unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetra-2-ethylhexyl phosphonium iodide tetrapropyl phosphonium iodide, methyltriphenyl phosphonium iodide, and the like; methylammonium iodide. tri-P-tolyl-ammonium iodide, decylammonium iodide. ethylphosphonium iodide triphenyl-phosphonium iodide. tricylcohexylphosphonium iodide, tri-p-tolyphosphonium iodide, and the like, with methyl iodide and hydrodic acid being preferred. Also useful are bromine and its corresponding compounds and chlorine and its corresponding compounds. Any source of halogen atom can be used provided that it does not have a deleterious effect on the reaction.

The amount of halogen charged is dependent upon the amount of rhodium employed. The halogen: rhodium mgm-atom ratio is generally from about 0.1:1 to 200:1, although greater or lesser amounts can be employed. It is prefered to employ a ratio from about 1:2 to about 100:1 and, most preferably, from about 1:1 to about 75:1.

The third component of the catalyst system is a phosphoruscontainng ligand of the formula R'R'PGZ, wherein R' and G are as previously defined and Z is selected from the group:

In a first embodiment, the phosphorus-containing ligand has the general formula

  (I)

wherein R' and G are as before. The R' groups can be alike, different or mixed. Typical ligands of this embodiment include:

(1) (C$_6$H$_5$)$_2$P—C$_2$H$_4$—P(=O)(C$_6$H$_5$)$_2$ (2) (C$_6$H$_5$CH$_2$)$_2$P—C$_3$H$_6$—P(=O)(CH$_2$C$_6$H$_5$)$_2$ (3) CH$_3$(CH$_2$)$_2$—P[(CH$_2$)$_2$CH$_3$]—C$_4$H$_8$—P(=O)[(CH$_2$)$_2$CH$_3$]—(CH$_2$)$_2$CH$_3$ (4) (4-CH$_3$C$_6$H$_4$)(CH$_3$C$_6$H$_4$)P—C$_5$H$_{10}$—P(=O)(CH$_2$CH$_3$)$_2$ (5) (C$_6$H$_5$)(CH$_3$CH$_2$C$_6$H$_4$)(CH$_3$)P—C$_2$H$_4$—P(=O)(C$_6$H$_5$)$_2$ (6) CH$_3$(CH$_3$)P—C$_2$H$_4$—P(=O)(CH$_3$)(CH$_3$)

(7) (C$_2$H$_5$)(C$_6$H$_5$)P—CH=CH—P(=O)(CH$_2$C$_6$H$_5$)(C$_3$H$_7$)

(8) (C$_6$H$_5$)$_2$P—CH(CH$_2$C(=O)CH$_3$)—CH$_2$—P(=O)(C$_6$H$_5$)$_2$

An especially preferred ligand of Formula (I) is

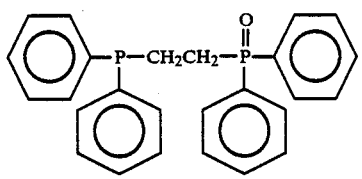

In a second embodiment the phosphorus-containing ligands have the general formula (II):

R'R'P(G)C(O)OR'' and in third embodiment the phosphorus-containing ligands have the general formula III:

$$\text{R'R'PGCR''} \atop \overset{O}{\underset{\|}{}}$$

wherein R' and G are as before; and R'' is R'

Typical examples of formula II compounds include:

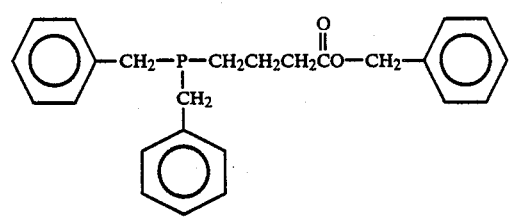 (a)

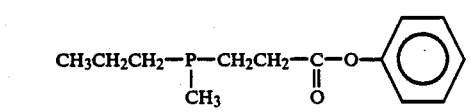 (b)

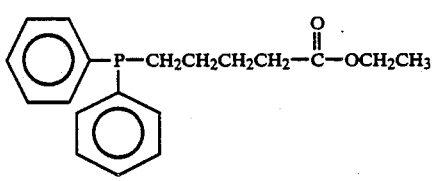 (c)

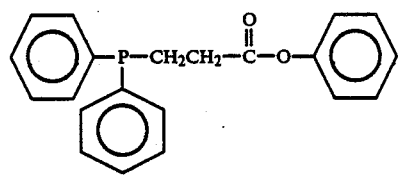 (d)

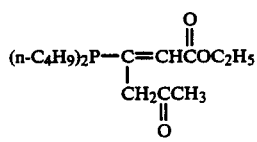 (e)

Typical examples of formula (III) compounds include:

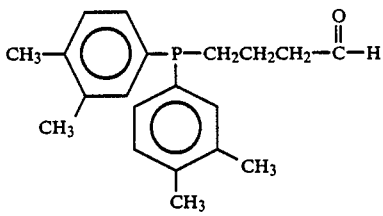 (f)

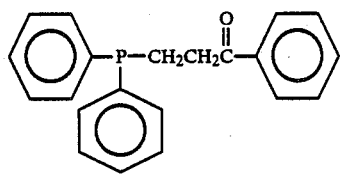 (g)

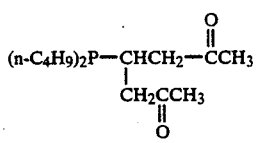 (h)

(n-C₄H₉)₂P—CHCH₂—ĈCH₃
          |         ‖
          CH₂CCH₃   O
              ‖
              O (i)

It has been found that conventional ligands such as ER₃ (E=P,N, As and R=organic moiety) and chelating agents, such as R'R'P(CH₂)ₙPR'R' tend to deactive the catalyst system at low temperature and pressure.

it is believed important that the oxo (O=) group of the —P(O)—; —C(O)O— or —C(O)— moiety of Z may be capable of becoming bonded to the rhodium atom in order to provide the activated catalyst which permits rapid reaction with CO and halogen promoter to enhance the rate of reaction.

The reactive rhodium complex of formula A can be generally prepared and isolated by the typical reaction involving the dissolution of [Rh(CO)₂Cl ]₂ , or any other halide compound of this formula, in an inert solvent such as dichloromethane benzene, toluene and like, under inert atmospheric conditions. A stoichiometric amount of phosphine, based on the rhodium content, is added, and the mixture is stirred at a temperature of from about 0° C. or less up to the boiling point of the mixture or higher. The reaction can be carried out at subatmospheric, atmospheric or superatmospheric pressure. The temperature and pressure are not critical.

Stirring is continued until the reaction is complete and this, as is obvious will be dependent upon the specific reactants employed, reaction conditions used and the size of the batch. At completion of the reaction one can, if so desired, separate the complex from the diluent using conventional procedures.

The structure of the formula A complex, identified herein as [A']is believed to be (schematically) as follows:

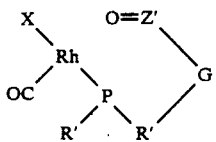

wherein R', G and X are as before and Z' is —P—R'R'; —COR" or —CR" and wherein R" is R'. The formula A complex may be formed in either the cis- or trans-geometrical isomer, wherein the X- and OC- moieties in complex A' are as they appear or are reversed.

Analysis to date of complex A' by NMR and IR has demonstrated the cis-isomer as the form present at room temperature.

In the catalytic reaction for the production of the esters the catalyst complex can be prepared and then added to the reactor or it can be formed in-situ during the reaction.

Carbon monoxide may be combined with Formula A complexes to form Formula B complexes. That complex may be represented, schematically by Formula B' as follows:

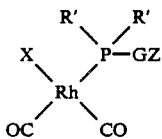

wherein X, R', G, and Z are as before.

If desired. Formula B complexes may be prepared in advance of the process by the carbonylation of Formula A complexes or the like. Formula B complexes have not yet been isolated, but, from spectral analyses of the reaction mixture appear to have the indicated structure. Other procedures which will be apparent to those skilled in this art may also be utilized to make Formula B complexes.

The concentration of ligand charged to the catalytic reaction can be varied from a molar ratio of ligand to rhodium of from about 5:1 to 1:5. preferably from 2:1 to 1:2 and most preferably about 1:1.

The reaction is carried out at a mild reaction temperatures, up to about 130° C. and preferably from about 40° C. to 120° C. and most preferably from 60° C. to 110° C.

The reaction pressure employed is much milder than those generally employed. The pressure of the reaction generally is up to about 250 psig and, preferably, from 50 psig to 150 psig.

The reaction time varies depending upon the reaction parameters, reactor size and charge, and the individual components employed at the specific process conditions The reaction can be a batch or continuous reaction.

The process may be carried out in any convenient equipment, for example, either a glass pressure bottle (Fisher Porter Bottle ®) or in a 300 c.c. reaction autoclave. In the case of the glass bottle degassed alcohol, as $CH_3OH$, and optionally, an alcohol of the formula R1 OH, containing a rhodium source; for example $[Rh(CO)_2Cl]_2$ and a phosphorus containing ligand; i.e. R'R'PG P(O)R'R' in the desired amounts were added under CO pressure to the bottle. Next a promoter, such as $CH_3I$. was added and the bottle was sealed by means of a valve and pressurized to 15 psig CO. The bottle was then heated to the desired reaction temperature by means of an oil bath at which point the pressure was adjusted to the reported value with CO. The bottle was repressurized after every 10 psig uptake.

After the desired temperature was reached the reaction was allowed to consume carbon monoxide for the time period indicated, usually from ½ to 5 hours. After the allotted reaction period the pressure bottle was cooled and the product mixture was transferred to a chilled bottle under $N_2$ subsequent analysis was performed using a Hewlett-Packard Model 5880 gas chromatograph equipped with a one-eighth inch diameter by ten feet long column packed with Chromosorb 101 or a Varian 3700 gas chromatograph equipped with a SUPELCO DB 1701 30M capillary column.

The following procedures are used with a 300 cc Hasteloy ® steel autoclave reactor equipped with temperature and pressure sensing means, electrical heating means, an internal cooling coil, magnetically driven agitator and inlet and outlet means for introducing and removing components from the reactor, prior to charging the reactants the autoclave are washed with methanol at 100° C. under a syn gas pressure of 500 to 1.000 psig by agitating for 30 minutes. The autoclave is drained, rinsed with dry acetone, and dried with nitrogen. The liquid components are charged to the cleaned autoclave first and then the solid components were added and stirred. The autoclave is closed, purged with carbon monoxide and then pressurized to the desired pressure, usually 20 to 30 psig with carbon monoxide. The autoclave contents are heated to the selected temperature generally between 50 and 100° C. with agitation (usually 750 rpm). in about 45 minutes. After the desired temperature is reached the reaction is allowed to consume carbon monoxide for the time period indicated, usually from ¼ to 5 hours. During this time the pressure is maintained by addition of carbon monoxide as needed.

At the end of the reactor run, the contents are cooled generally to about 10° C. A vapor phase sample is taken for gas chromatography analysis: the gas phase is vented through two dry-ice acetone traps and then through a 10 liter saturated solution of calcium hypochorite to remove metal carbonyls, if formed. The reactor is pressurized three times with nitrogen. 90 psig and vented through the same system. The residual reactor contents are dumped into a chilled pressure bottle and sealed. Analysis is as for the pressure bottle procedure.

The following examples serve to further illustrate this invention.

EXAMPLE 1

A Fisher Porter Bottle ® was charged with the following components:

| | |
|---|---|
| $[Rh(CO)_2Cl]_2$ | 0.09 gm (0.46 millimoles) |
| $Ph_2PCH_2CH_2P(O)Ph_2$ | 0.2 gm (0.48 millimoles) |
| $CH_3I$ | 2.28 gm |
| $CH_3OH$ | 4.4 gm |

In the ligand formula, Ph represents a phenyl group. The bottle was sealed pressured to 1psi CO. then heated to 80° C. At 80° C. the pressure was adjusted to 75 psi with CO and the bottle was repressurized after every 10 psig CO uptake. The reaction was carried out for 2.0 hr. The products and their approximate amounts were as follows (excluding water):

| Product | Moles |
|---|---|
| Methanol | 0.044 |
| Methyl iodide | 0.012 |
| Methyl acetate | 0.043 |
| Acetic acid | 0.0085 |

No other products were detected. The calculated rate to methyl acetate (including acetic acid equivalents) is 4.3 Mhr$^{-1}$ and the selectivity approaches 100%. The methanol conversion is 70%.

Similar results are obtained when other rhodium sources are substituted; such as $Rh_2(CO)_4Br_2$, $Rh(CO)_2AcAc^*$. $K_4Rh_2I_2(SnI_2)_4$, $[(n-C_4H_9)_4N][Rh(CO)_2I_2]$.

* AcAc = acetylacetonate

EXAMPLE 2

Six runs were carried out in accordance with Example 1, except $Ph_2PCH_2CH_2P(O)Ph_2$ was not utilized. In each run the rhodium concentration was 0.071 M; $CH_3I$:Rh ratio was 17:1; temperature was 80° C. and total operating pressure was 80 psig. The runs were carried out for 2–4 hours. The rate in moles/hour is the total of methyl acetate rate and acetic acid rate. The results are summarized in Table 1.

TABLE 1

| Catalyst Precursor | Rate MHr$^{-1}$ |
|---|---|
| (a) $[Rh(CO)_2Cl]_2$ | 0.05 |
| (b) $Rh(CO)_2AcAc$ | 0.1 |
| (c) $[Rh(CO)_2Cl]_2 + 2PPh_3$ | 0.05 |
| (d) $[Rh(CO)_2Cl]_2 + 2Ph_2(CH_3)P$ | 0.07 |
| (e) $[Rh(CO)_2Cl]_2 + 2Ph_2PCH_2CH_2PPh_2$ | 0.0 |
| (f) $[Rh(CO)_2Cl]_2 + 2Ph_2P(O)CH_2CH_2P(O)Ph_2$ | 0.03 |

Runs (a) and (b) are similar to those in U.S. Pat. No. 3,769,329 and show that at low temperature and low pressure, the productivities are very low. Runs (c) and (d) are similar to U.S. Pat. No. 4,212,989 and show addition of $ER_3$ is not beneficial. Run (e) is analogous to GB Pat. No. 1,584,740 which, under our conditions is totally inactive. Run (f) demonstrates that the bis-oxide phosphine ligand $Ph_2P(O)CH_2CH_2P(O)Ph_2$ is also ineffective.

EXAMPLE 3

Five runs were carried out according to Example 1 utilizing various ligands of formula I wherein the reaction time was maintained at 1.5 hours. The product distribution was similar to that of Example 1. The results are summarized below:

| Run | [Rh]$^a$ M/L$^c$ | [CH$_3$I] M/L | Ligand [L] | [L] Moles | Rate$^b$ Mhr$^{-1}$ |
|---|---|---|---|---|---|
| 1 | 0.071 | 1.2 | $Ph_2PCH_2P(O)Ph_2$ | 0.071 | 0.1 |
| 2 | 0.071 | 1.2 | $Ph_2P(CH_2)_2P(O)Ph_2$ | 0.142 | 0.7 |
| 3 | 0.071 | 1.2 | $Ph_2P(CH_2)_3P(O)Ph_2$ | 0.071 | 2.4 |
| 4 | 0.071 | 1.2 | $Ph_2P(CH_3)_4P(O)Ph_2$ | 0.071 | 2.6 |
| 5 | 0.071 | 1.2 | $Ph_2P(CH_2)_2\overset{O}{\overset{\|}{C}}OCH_2CH_3$ | 0.071 | 2.6 |

$^a$Rh charged as $[Rh(CO)_2Cl]_2$
$^b$Rate is the total of methyl acetate rate and acetic acid rate.
$^c$M/L is moles per liter The data demonstrates that for the ligand $Ph_2O(CH_2(_nP(O)Ph_2$ a value of n=1 is deterimental for catalysis. In run 2 where the ligand: rhodium ratio was 2:1, the rate was slower than in Example 1 where the ligand: rhodium rate was about 1:1.

Similar results are found when a preformed complex A is substituted for the in-situ formed catalyst.

EXAMPLE 4

The reaction was carried out in accordance with the procedure of Example 1 except the amount of methanol used was 3:84 gms and 0.78 gms of ethanol was added. This represents a molar ratio of $CH_3OH$:$CH_3CH_3OH = 7.06:1$. The reaction time was 0.4 hr. The liquid produces (excluding water) were:

| Product | Wt % |
|---|---|
| Methanol | 39.9 |
| Methyl iodide | 7.5 |
| Ethanol | 12.3 |
| Methyl Acetate | 34.8 |
| Ethyl iodide | 0.2 |
| Ethyl Acetate | 8.3 |
| Acetic Acid | Trace |

This run demonstrates that ethyl acetate can be obtained from a feedstock of $CH_3OH$ and $CH_3CH_2OH$.

EXAMPLE 5

The reaction was carried out in accordance with the procedure of Example 4 except that the reaction time was 3.0 hrs. The liquid products were (excluding $H_2O$):

| Product | Wt % |
|---|---|
| Methanol | 1.8 |
| Methyl iodide | 8.9 |
| Ethanol | 2.8 |
| Methyl Acetate | 33.6 |
| Ethyl iodide | 1.8 |
| Ethyl Acetate | 27.5 |
| Acetic Acid | 23.0 |

This run demonstrates that at longer reaction times a higher amount of ethyl acetate can be obtained. It is believed that many equilibria exist in this system such as:

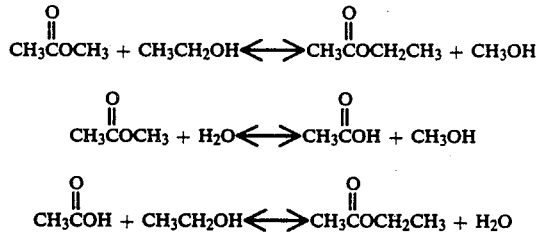

It is postulated that this run has most likely achieved its eguilibrium after 3.0 hours. If desired, the products such as methyl acetate/acetic acid can be recycled back to the reaction after ethyl acetate is separated. Other promoters such as hydriodic acid, ethyl iodide, methyl bromide, can be substituted for methyl iodide with similar results.

EXAMPLE 6

The reaction was carried out in accordance with procedure of Example 4 (run time = 1.3 hr.) except the following amounts were used: $CH_3OH = 2.3g$. and CH₃CH₂OH = 1.38 gm. This corresponds to a CH₃OH:CH₃CH₂OH molar ratio of 2.4:1. Excluding water, the liquid products were:

| Product | Wt % |
| --- | --- |
| Methanol | 15.9 |
| Methyl iodide | 6.4 |
| Ethanol | 24.0 |
| Methyl Acetate | 28.4 |
| Ethyl iodide | 1.4 |
| Ethyl Acetate | 21.0 |
| Acetic Acid | 1.7 |

The results illustrate that as the methanol: higher alcohol mole ratio approaches about 2:1, enhanced amounts of higher alcohol are substituted on the acetate moiety by transesterification of the methyl acetate. When other ligands as set forth herein are substituted for the ligand of Example 4. similar results are obtained.

EXAMPLE 7

PREPARATION OF COMPLEXES

A series of runs was performed using the following general procedure to produce the complexes of formulas A' and B'.

A solution of 2.5 millimoles (mm) of C₆H₅PCH₂P(O)C₆H₅)₂ in 10ml methylene chloride was added to a solution of 1.25 mm [Rh(CO)₂Cl]₂ in 10ml methylene chloride. The mixture was allowed to stir for 10 minutes and the methylene chloride was removed under vacuum. The residual viscous oil was redissolved in 10 ml methylene chloride and the solvent evaporated again. This procedure was repeated three to four times.

The residue from the final evacuation was dissolved in 5 ml methylene chloride. Yellow crystals precipitated upon standing. The crystals were filtered, washed with methylene chloride and dried under vacuum. X-ray crystallographic analysis showed that the compound corresponds to:

cis-RhCl(CO)[(C₆H₅)₂PCH₂O(O)(C₆H₅)₂]·CH₂Cl₂, which contains a Rh to O bond. The infrared spectrum displayed a single intense bond at 1990 cm⁻¹ due to the presence of coordinated CO to Rh in the complex.

The above procedure was followed exactly using (C₆H₅)₂P(CH₂)ₙP(O)(C₆H₅)₂; in which n was 2, 3 and 4 and for (C₆H₅)₂P(CH₂)ₙC(O)OC₂H₅ in which n was 2. In all instances yellow crystals were recovered which gave infrared spectra similar to the first complex described above, having an intense band at 1990 cm⁻¹ indicating the formation of the similar structure. The complex products produced had the formulas:

cis-RhCl(CO)[(C₆H₅)₂PC₂H₄P(O)(C₆H₅)₂]

cis-RhCl(CO)[(C₆H₅)₂PC₃H₆P(O)(C₆H₅)₂]

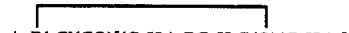

cis-RhCl(CO)[(C₆H₅)₂PC₄H₈P(O)(C₆H₅)₂]

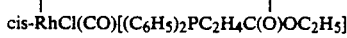

cis-RhCl(CO)[(C₆H₅)₂PC₂H₄C(O)OC₂H₅]

The dicarbonyl compounds of the above were prepared by reacting a portion of each of the above monocarbonyl compounds, respectively under CO pressure. Infrared spectra showed the formation of the dicarbonyl compounds had been achieved by the presence of two intense bands, typically at 2090 cm⁻¹ and 2010 cm⁻¹.

The experimental findings are unexpected in view of the disclosure by R. T. Eby and T. C. Singleton in "Applied Industrial Catalysis", Vol. I, Chapter 10, page 281, Academic Press, NYC (1983). In Chapter 10, entitled "Methanol Carbonylation to Acetic Acid", the authors state: "Iodide salts of alkali metals are inactive as catalysts in the rhodium-catalyzed carbonylation of methanol, even though the [Rh(CO)₂I₂]—complex is formed in the presence of alkali metal iodides."

I claim:

1. Process for the production of a mixture of methyl acetate and ethyl acetate which comprises catalytically reacting a mixture of methanol and ethanol, and carbon monoxide in contact with a homogeneous catalyst system consisting essentially of (a) a rhodium component selected from the group consisting of rhodium metal and a rhodium compound, (b) a phosphorus containing ligand

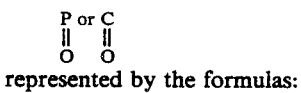

represented by the formulas:

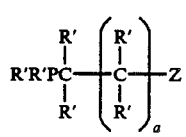

(V)

or

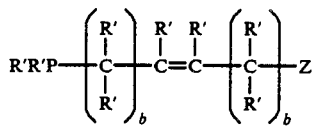

(VI)

and (c) a halogen containing compound as a promoter, wherein R' is —H or an aryl, aralkyl or alkaryl group having from 6 to 10 ring carbon atoms and the alkyl moiety of said aralkyl or alkaryl group having from 1 to 10 carbon atoms, or an alkyl group having from 1 to 10 carbon atoms, and wherein one or more of said R' groups can be substituted with a Z group but where no more than 3 of said R' groups in the molecule are so substituted, where a is an integer from 0 to 4, b is an integer from 0 to 3, and Z is a member selected from the group consisting of:

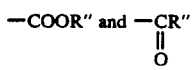

—COOR" and —CR"
                    ‖
                    O wherein R" is R' and said reaction is carried out at a reaction temperature of up to about 130° C. and a reaction pressure of up to about 250 psig.

2. The process as claimed in claim 1 wherein the ligand is Ph₂P(CH₂)COOCH₂CH₃, wherein Ph is phenyl.

* * * * *

UNITED STATES PATENT AND TRADEMARK OFFICE
CERTIFICATE OF CORRECTION

PATENT NO. : 4,990,654

DATED : February 5, 1991

INVENTOR(S) : R.W. Wegman

It is certified that error appears in the above-identified patent and that said Letters Patent is hereby corrected as shown below:

Column 3, lines 3-4, should read -- Rh-I catalyst. In several examples, notably Examples 27-29, a pro- --.

Column 3, line 24, "rCac-" should read --reac- --.

Column 4, line 43, "Rh(CO)X(R'R'(GZ)" should read -- Rh(CO)X(R'R'PGZ) --.

Column 5, line 65, "therof" should read -- thereof --.

Column 6, line 36, "$RhCl_3.H_2O$" should read -- $RhCl_3.3H_2O$ --.

Column 6, line 37, "$RhCl_3.H_2O$" should read -- $RhBr_3.3H_2O$ --.

Column 6, line 43, should read -- $Rh(NO_3)_3$ --.

Col. 6, line 44, should read --$[(n-C_4H_9)_4N][Rh(CO)_2X_2]$ where X = Cl-,--

Column 6, between lines 49 and 50, insert -- $K_4Rh_2Cl_2(SnCl_2)_4$ --.

Column 6, line 62, "ar" should read -- are --.

Column 7, line 19, after "sodium iodide" insert -- , --.

Column 7, line 20, after "ethyl iodide" insert -- , --.

Column 7, line 20, after "propyl iodide" insert -- , --.

Column 7, line 21, after "n-decyl iodide" insert -- , --.

Column 7, line 21, after "acetyl iodide" insert -- , --.

UNITED STATES PATENT AND TRADEMARK OFFICE
CERTIFICATE OF CORRECTION

PATENT NO. : 4,990,654

DATED : February 5, 1991

INVENTOR(S) : R.W. Wegman

It is certified that error appears in the above-identified patent and that said Letters Patent is hereby corrected as shown below:

Column 7, line 23, "R'''4NI" should read -- $R'''_4NI$ --.

Column 7, line 25, after "unsaturated" insert -- , --.

Column 7, line 26, after "aryl" insert -- , --.

Column 7, line 31, after "iodide" insert -- , --.

Column 7, line 35, after "phosphonium iodide" insert -- , --.

Column 7, line 52, "phoruscontainng" should read -- phorus-containing --.

Column 11, lines 60-61, "R1 OH" should read -- $R_1OH$ --.

Column 12, line 8, "$N_2$ subsequent" should read -- $N_2$. Subsequent --.

Col. 13, line 55, in the Table, "Liqqand [L]" should read --Ligand [L]--

Column 13, line 67, "$Ph_2O(CH_2(_nP(O)Ph_2$" should read -- $Ph_2P(CH_2)_nP(O)Ph_2$ --.

Column 14, line 58, "eguilibrium" should read -- equilibrium --.

Column 15, line 45, "cis-RhCI(CO)[$(C_6H_5)_2PCH_2O(O)(C_6H_5)_2$.$CH_2-CI_2$" should read -- cis-RhCI(CO)[$(C_6H_5)_2PCH_2P(O)(C_6H_5)_2$].$CH_2-CI_2$ --.

Col. 16, line 30, delete "P or C".

```
        11    11
         O     O
```

UNITED STATES PATENT AND TRADEMARK OFFICE
CERTIFICATE OF CORRECTION

PATENT NO. : 4,990,654
DATED : February 5, 1991
INVENTOR(S) : R. W. Wegman

It is certified that error appears in the above-indentified patent and that said Letters Patent is hereby corrected as shown below:

Column 16,

Claim 2, line 2, "$Ph_2P(CH_2)COOCH_2CH_3$" should read -- $Ph_2P(CH_2)_2COOCH_2CH_3$ --

Signed and Sealed this

Twenty-second Day of March, 1994

Attest:

BRUCE LEHMAN

Attesting Officer

Commissioner of Patents and Trademarks